United States Patent [19]
Brugh

[11] Patent Number: 5,869,061
[45] Date of Patent: Feb. 9, 1999

[54] PROTECTIVE HAND LOTION OF ALOE VERA GEL AND VITAMIN E GEL

[76] Inventor: Bettie Sue Brugh, 537 West Wood Blvd. NW., Roanoke, Va. 24017

[21] Appl. No.: 827,089

[22] Filed: Mar. 27, 1997

Related U.S. Application Data

[60] Provisional application No. 60/018,918 Jun. 4, 1996.

[51] Int. Cl. $^6$ .................................................. A01N 65/00
[52] U.S. Cl. ............................................................ 424/195.1
[58] Field of Search ........................................... 424/195.1

[56] References Cited

U.S. PATENT DOCUMENTS

| | | | |
|---|---|---|---|
| 4,389,418 | 6/1983 | Burton | 514/785 |
| 4,832,858 | 5/1989 | Vishnupad et al. | 508/110 |
| 4,857,328 | 8/1989 | Trenzeluk | 424/195.1 |
| 4,980,084 | 12/1990 | Vishnupad et al. | 252/309 |
| 5,208,013 | 5/1993 | Klein | 424/59 |
| 5,252,331 | 10/1993 | Curtis et al. | 424/401 |

FOREIGN PATENT DOCUMENTS

| | | |
|---|---|---|
| 58853 | 1/1982 | European Pat. Off. . |
| 2138679 | 10/1984 | United Kingdom . |
| 84/02845 | 8/1984 | WIPO . |

OTHER PUBLICATIONS

Strianse, S.J. In "Cosmetics: Science and Technology". vol. 1, 2nd ed. (1972) (Wiley: New York) pp. 179–222, 1972.
Johnson's Baby Lotion Label, Johnson & Johnson, 1996.

*Primary Examiner*—Jean C. Witz
*Assistant Examiner*—Susan Hanley
*Attorney, Agent, or Firm*—Richard C. Litman

[57] ABSTRACT

The invention relates to a protective hand lotion composition and method of use wherein the lotion consists of aloe vera gel, vitamin E gel, petroleum jelly, quaternary ammonium salt, fatty acids, fatty acid esters, mineral oil, dimethylpolysiloxane, water and other ingredients. The composition is applied to the hands, protects the hands from irritating materials and provides softened and smoothly textured skin.

2 Claims, No Drawings

PROTECTIVE HAND LOTION OF ALOE VERA GEL AND VITAMIN E GEL

CROSS-REFERENCE TO RELATED APPLICATION

This application claims the benefit of U.S. Provisional patent application Ser. No. 60/018,918, filed Jun. 4, 1996.

BACKGROUND OF THE INVENTION

1. Field of the Invention

The present invention is directed to a hand and skin lotion composition and method of use. More particular, this invention relates to a protective hand lotion comprising a mixture of aloe vera gel, vitamin E gel, quaternary ammonium salt, petroleum jelly, water, propylene glycol, fatty acids and other ingredients.

2. Description of Related Art

Earlier patents for lotions and other emulsions do not teach the instant combination of aloe vera gel, petroleum jelly, and vitamin E gel. Furthermore, they do not contemplate the aforesaid mixture mixed with a quaternary ammonium salt.

U.S. Pat. No. 4,832,858 to Vishnupad et al. shows a water dispersible petroleum jelly formulation comprising an emulsion made by ultrasonic emulsification.

U.S. Pat. No. 4,389,418 to Burton shows the use of a quaternary ammonium salt in a skin preparation with petrolatum or mineral oil, water and other ingredients.

U.S. Pat. No. 4,857,328 to Trenzeluk describes the use of a specially prepared aloe vera composition in a skin preparation for alleviating certain skin conditions.

U.S. Pat. No. 4,980,084 to Vishnupad et al. discloses water rinsable petroleum jelly compositions comprising a water-in-oil emulsion of petroleum jelly, mineral oil, and a surface active detergent.

The U.S. Pat. No. 5,208,013 to Klein describes a skin preparation comprising water, dimethicone, stearic acid, coconut fatty acid, other ingredients, and aloe vera gel and vitamin E. The principal function of the composition is to provide a barrier against irritation of the skin from harmful materials.

United Kingdom Pat. No. 2,138,679 shows a skin preparation comprising mixtures of banana oil, aloe vera gel and vitamin E in minor amounts.

None of the above inventions and patents, taken either singly or in combination, is regarded as describing the instant invention as claimed.

SUMMARY OF THE INVENTION

The present invention provides, in one embodiment, a unique emulsion composition or lotion for use primarily on the skin of the hands comprising a mixture of aloe vera gel, petroleum jelly, vitamin E gel, water, a quaternary ammonium salt, propylene glycol, fatty acids and other ingredients. The present invention satisfies the need for an effective hand lotion that keeps the hands feeling and looking healthy, and which provides a long lasting barrier to the deleterious effects of institutional and household cleaning and maintenance compositions. Additionally, the hand lotion protects hands from the abrasive action of using the hands in ordinary housekeeping operations such as the changing of bed linens.

Accordingly, it is a principal object of the invention to provide a hand lotion comprising aloe vera gel, vitamin E gel and other ingredients having beneficial effects upon the skin, enabling the skin to maintain a soft and smooth texture and a healthy appearance.

It is another object of the invention to provide a hand lotion functioning as a barrier against the irritating effects on the skin of the hands of household and institutional cleaning and maintenance compositions.

It is a further object of the invention to provide a protective hand lotion that will not easily wash off as a result of normal hand washing procedures, thus maintaining its protective action for normal eight hour work periods, for example.

Still another object of the invention is to provide a hand lotion for the professional institutional maintenance worker which is low in cost and possesses enhanced protective ability.

It is an object of the invention to provide improved elements and arrangements thereof in a composition for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENTS

The present invention comprises a skin lotion composition which includes aloe vera gel, vitamin E gel, a quaternary ammonium salt, water, fatty acids, propylene glycol, mineral oil and petroleum jelly.

More specifically, it has been found that a composition comprising major amounts of water, propylene glycol, cetyl palmitate, fatty-acids, particularly stearic acid and oleic acid, quaternary ammonium salt, aloe vera gel, petroleum jelly and vitamin E gel provides an effective hand and skin lotion composition.

The aloe vera gel used is comprised of 99 percent by weight aloe vera extract and about 1% by weight of other ingredients, such as propylene glycol, triethanolamine and DMDM Hydantoin. However, substantially pure aloe juice, as it is extracted from the leaves of an aloe plant, is known to be a gel-like material, and is usable in my composition, and is functionally equivalent to 99% aloe gel compositions sold in drug stores.

The vitamin E gel used comprises 99% by weight di-alpha tocopherol acetate and a small amount of thickening agent.

More specifically, the composition of my invention is comprised of:

(A) about 70 to 87 percent by volume based on the total volume or (v/v) wt % of the composition at normal ambient room temperatures of the following ingredients: water, propylene glycol, cetyl palmitate, myristyl myristate, a quaternary ammonium salt such as, for example, dimethyl distearyl ammonium chloride, glyceryl stearate, stearic acid, oleic acid, polyoxyethylene (4) sorbitan mono stearate, a fully methylated linear siloxane polymer such as dimethylpolysiloxane, isopropyl palmitate, cetyl ricinoleate, steroxymethylsilane, sorbitan stearate, mineral oil, synthetic beeswax, carbomer, which is a homopolymer of acrylic acid crosslinked with an allyl ether of pentaerythritol such as, for example, Carbopol 910, 934 or 940, made by B. F. Goodrich Co., disodium ethylene diamine tetra acetic acid (EDTA), and minor amounts of functional adjuncts such as fragrance, methylparaben, BHT and a suitable dye;

(B) from about 6.5 to about 8 (v/v) wt % of petroleum jelly;

(C) from about 6.5 to about 8 (v/v) wt % of aloe vera gel; and (D) from about 2.2 to about 12 (v/v) wt % vitamin E gel.

Materials identified herein by trade name or names of trade are known, the chemical composition of which may be determined from referring to the International Cosmetic Dictionary, published by the Cosmetic, Toiletry and Fragrance Association, 1101 17th St., Washington, D.C., 20036, edited by John A Wenninger, L. of C. No. TP983.C95.

The ratio by weight of the ingredients comprising the portion of the composition identified above as (A) are such as to provide a creamy, flowable, stable emulsion composition, the major amount of the composition comprising water. The other ingredients are to be used in proportional amounts to be effective for their intended function. For example, the quaternary ammonium salt emulsifier should be in the range of about 4 percent by weight of portion (A), comprising a significant amount of the ingredients other than the water.

It has been observed that the composition identified as (A) in the above description does not provide an equivalently long lasting protection if the ingredients (B), (C) and (D) are not included, but that when all of the materials identified (A), (B), (C) and (D) are together in the proportions disclosed above and herein, an enhanced protective barrier is accomplished. For example, hands may be washed at least three times using normal washing methods of soap or detergent and water without loss of the protective benefits provided by the present lotion.

The composition may be prepared in a conventional manner. The ingredients comprising portion (A) of my composition are mixed together under conditions and in suitable proportions as to provide a smooth, creamy, stable emulsion. Ingredients (B), (C) and (D) are measured by volume, placed together with portion (A) in a suitable container and heated while mixing with a suitable mixing instrument. The composition is heated to allow ingredients present in the form of a semi-solid, such as, for example, petroleum jelly, to be able to flow and mix with all the other ingredients. The temperature used in the heating process should be substantially below 212 degrees F. or 100 degrees C., merely sufficient to liquify all of the materials used such as, for example, about 140 degrees F.

EXAMPLE 1

Exactly twelve - 9 oz. bottles of product are made as follows: warm 90 oz. of Johnson & Johnson baby lotion (conveniently, 10 - 9 oz. bottles) to about 110 degrees F. This will be sufficiently warm to melt down the petroleum jelly to be added. Stir in 20 slightly heaped tablespoons of Vaseline Petroleum Jelly (9 oz.), 20 tablespoons of vitamin E gel (8 oz.), and 30 tablespoons of aloe vera gel. Stir into a smooth mixture.

EXAMPLE 2

Employ the ingredients of Example 1, but eliminate the baby lotion completely. Stir the remaining three ingredients together and simultaneously at a temperature of about 110 degrees F. until a smooth mixture is obtained. Increase the amounts, proportionally of course, to produce a desired quantity of product.

The method of use is conventional. A suitable amount of the lotion is taken up in the hands and they are rubbed together to fully coat the skin of the hands with the lotion.

The foregoing examples are intended to illustrate the preferred embodiments of the invention but should not be construed in a limiting sense. It is to be understood that the present invention encompasses any and all embodiments within the scope of the following claims.

I claim:

1. A hand and skin lotion composition effective as a skin softening agent and barrier against skin irritants, consisting of:
    a) 70 to 88 (v/v) wt % of a composition consisting of: water, propylene glycol, cetyl palmitate, myristyl myristate, glyceryl stearate, stearic acid, oleic acid, polyoxyethylene (4) sorbitan monostearate, dimethylpolysiloxane, isopropyl palmitate, cetyl ricinoleate, mineral oil, dimethyl distearyl ammonium chloride, stearoxymethylsilane, sorbitan stearate, synthetic beeswax and carbomer;
    b) 3.5 to 8.5 (v/v) wt % petroleum jelly;
    c) 6.5 to 12 (v/v) wt % aloe vera gel; and
    d) 2.0 to 12.5 (v/v) wt % vitamin E gel.

2. A hand and skin lotion composition effective as a skin softening agent and barrier against skin irritants, consisting of:
    a) 70 to 88 (v/v) wt % of a composition consisting of: water, propylene glycol, cetyl palmitate, myristyl myristate, glyceryl stearate, stearic acid, oleic acid, polyoxyethylene (4) sorbitan monostearate, dimethylpolysiloxane, isopropyl palmitate, cetyl ricinoleate, mineral oil, dimethyl distearyl ammonium chloride, stearoxymethylsilane, sorbitan stearate, synthetic beeswax, carbomer, fragrance, preservative and dye;
    b) 3.5 to 8.5 (v/v) wt % petroleum jelly;
    c) 6.5 to 12 (v/v) wt % aloe vera gel; and
    d) 2.0 to 12.5 (v/v) wt % vitamin E gel.

* * * * *